(12) United States Patent
Reeves et al.

(10) Patent No.: US 6,369,293 B1
(45) Date of Patent: Apr. 9, 2002

(54) ABSORBENT COMPOSITION INCLUDING AN UNCROSSLINKED POLYMER

(75) Inventors: William Grover Reeves, Appleton, WI (US); William Galey Robertson, Chelsea, MA (US); Mary Jeanne Dupuis, Kalamazoo, MI (US); Eric Scott Kepner, Fletcher, NC (US); Thomas Patrick Jorgenson, Neenah, WI (US); Gerald Lee Richmond, Clarkesville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/395,702

(22) Filed: Sep. 14, 1999

(51) Int. Cl.[7] .......................... A61F 13/15; C08G 3/00; C08F 6/00

(52) U.S. Cl. ...................... 604/372; 528/481; 528/491; 528/495; 528/496; 528/499; 528/502; 528/503; 428/304.4; 428/308.4; 524/81; 524/356; 604/358; 604/385.23

(58) Field of Search ................. 528/481, 491, 528/495, 496, 499, 502, 503; 428/304.4, 308.4; 524/81, 356; 604/358, 372, 385.23

(56) References Cited

U.S. PATENT DOCUMENTS

| | | |
|---|---|---|
| 3,377,261 A | 4/1968 | Ancker |
| 3,547,792 A | 12/1970 | Patterson |
| 3,664,343 A | 5/1972 | Assarsson |
| 3,783,872 A | 1/1974 | King |
| 3,814,101 A | 6/1974 | Kozak |
| 4,950,264 A | 8/1990 | Osborn, III |
| 5,589,545 A | 12/1996 | Ramachandran et al. |
| 5,700,872 A | 12/1997 | Wang et al. |
| 5,807,930 A | 9/1998 | Wang et al. |
| 5,948,829 A | * 9/1999 | Wallajapet et al. ........... 521/64 |
| 5,985,434 A | * 11/1999 | Qin et al. ................ 428/315.5 |

FOREIGN PATENT DOCUMENTS

| | | |
|---|---|---|
| EP | 0 484 952 A1 | 5/1992 |
| EP | 0 253 566 B1 | 3/1993 |
| EP | 0 537 683 B1 | 1/1997 |
| WO | WO 98/10928 A1 | 3/1998 |

OTHER PUBLICATIONS

Patent Abstracts of Japan JP 408333461A: Description of M.I. Kotoura et al., "Biaxially Oriented Polyester Film."
Shalaby, S.W. et al., Editors, *Water–Soluble Polymers,* ACS Symposium Series 467, 1991, Chapter 1, "Sturctural Design of Water–Soluble Copolymers," and Chapter 15, "Role of Labile Cross–Links in the Behavior of Water–Soluble Polymers."

* cited by examiner

*Primary Examiner*—Samuel A. Acquah
(74) *Attorney, Agent, or Firm*—Sebastian Pugliese, III

(57) ABSTRACT

An absorbent composition comprising an uncrosslinked, high molecular weight polymer, wherein the uncrosslinked, high molecular weight polymer is treated by a means to effectively insolubilize the uncrosslinked, relatively high molecular weight polymer such that the absorbent composition exhibits desirable absorbent properties. In particular, the absorbent composition has the ability to absorb a large quantity of liquid. The absorbent composition is useful in disposable absorbent products, such as those disposable absorbent products that are used to absorb bodily liquids. Suitable polymers include polyethylene oxide, poly(acrylic acid), poly(vinyl alcohol), and poly(vinyl pyrrolidone) wherein the polymer has a weight average molecular weight that is greater than about 1,000,000.

36 Claims, No Drawings

ABSORBENT COMPOSITION INCLUDING AN UNCROSSLINKED POLYMER

BACKGROUND OF THE INVENTION

The use of absorbent materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, preferably of about 20, and often of up to 100 times their weight in a test liquid, such as water or a saline solution. Clearly, incorporation of such absorbent materials in personal care products can reduce the overall bulk while increasing the absorbent capacity of such products.

A wide variety of materials has been described for use as absorbent materials in personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitrile. One characteristic common among such absorbent materials is that they are water-swellable and water-insoluble. In order to achieve such a water-swellable, water-insoluble characteristic, the absorbent material will generally be crosslinked. The amount of crosslinking will generally be above a minimum amount sufficient to make the material water-insoluble but also below some maximum amount so as to allow the material to be sufficiently water swellable so that the water-swellable, water-insoluble material absorbs a desired amount of liquid.

Crosslinking of a material may generally be achieved by either of two different types of crosslinking agents. The first type of crosslinking agent is a polymerizable crosslinking agent. Suitable polymerizable crosslinking agents are generally reactive to a monomer or monomers used to prepare the material and, thus, generally comprise at least two functional groups that are capable of reacting with the monomers. The second type of crosslinking agent is a latent crosslinking agent. Latent crosslinking agents generally do not take part in an overall polymerization process but, instead, are reactive to a polymer at a later point in time when a proper crosslinking condition is provided. Suitable post treatment conditions include using heat treatment, exposure to high energy radiation such as ultraviolet light, x-rays, beta-rays, or gamma-rays, exposure to microwaves, steam or high humidity treatment, high pressure treatment, or treatment with an organic solvent.

Such crosslinking processes inherently result in the use of a separate crosslinking agent or reaction condition thereby increasing the costs of manufacturing the chemically crosslinked material. Additionally, the use of certain crosslinking agents typically requires specialized handling procedures, further increasing the costs of manufacturing, and potentially limiting the applications for which the chemically crosslinked material may be used. Another disadvantage concerning the use of chemical crosslinking agents is that they are often based on chemicals which exhibit certain degrees of toxicity.

SUMMARY OF THE INVENTION

In one aspect, the present invention concerns an absorbent composition comprising an uncrosslinked polymer wherein the absorbent composition is able to absorb or immobilize a relatively large quantity of the liquid.

One embodiment of the present invention concerns an absorbent composition comprising an uncrosslinked polymer, wherein the uncrosslinked polymer has a weight average molecular weight greater than about 1,000,000 and wherein the absorbent composition exhibits a Free Swell value that is at least about 15 grams of water per gram of absorbent composition and a Centrifuge Retention Capacity value that is at least about 8 grams of water per gram of absorbent composition, wherein the time period used to determine both the Free Swell value and the Centrifuge Retention Capacity value is about 19 hours.

In another aspect, the present invention concerns a process for preparing an absorbent composition comprising an uncrosslinked polymer, wherein the absorbent composition exhibits desired absorbent properties.

One embodiment of the present invention concerns a process for preparing an absorbent composition comprising an uncrosslinked polymer, the process comprising the following steps:

a. preparing a mixture of a solvent soluble, uncrosslinked polymer that has a molecular weight greater than about 1,000,000 and a solvent in which the uncrosslinked polymer is soluble, wherein the soluble, uncrosslinked polymer dissolves into the solvent; and b. recovering the uncrosslinked polymer from the mixture, wherein the absorbent composition exhibits a Free Swell value that is at least about 15 grams of water per gram of absorbent composition and a Centrifuge Retention Capacity value that is at least about 8 grams of water per gram of absorbent composition, wherein the time period used to determine both the Free Swell value and the Centrifuge Retention Capacity value is about 19 hours.

In another aspect, the present invention concerns a disposable absorbent product comprising an absorbent composition of the present invention that exhibits desired absorbent properties.

In one embodiment of the present invention, a disposable absorbent product comprises a liquid-permeable topsheet, a backsheet attached to the topsheet, and an absorbent structure positioned between the topsheet and the backsheet wherein the absorbent structure comprises an uncrosslinked polymer of the present invention.

DETAILED DESCRIPTION OF THE PREFERRED EMBODIMENTS

The present invention relates to an absorbent composition comprising an uncrosslinked, high molecular weight polymer, wherein the absorbent composition exhibits desirable absorbent properties. Specifically, the present invention relates to an absorbent composition having the ability to absorb or immobilize a large quantity of liquid. The absorbent composition is useful in disposable absorbent products, such as those disposable absorbent products that are used to absorb or immobilize bodily liquids.

The present invention also provides an absorbent composition that absorbs or immobilizes a liquid with about the same final capacity as compared to commercially available synthetic, crosslinked superabsorbent materials. In one embodiment of the present invention, an absorbent composition is provided which spontaneously degrades over time so that the absorbent composition offers environmental advantages in comparison to existing absorbent compositions.

As used herein, the term "immobilant", "immobilize", or other similar terms, is intended to refer to a material, or the effects of such a material, that impedes the movement or flow of a liquid. In the present invention, an effectively entangled, solvent-insoluble uncrosslinked, relatively high molecular weight polymer is generally believed to act as an immobilant for many liquids, by which a liquid becomes entrapped within the network of entangled polymer chains, as well as an absorber of the liquid. Whether an effectively entangled, solvent-insoluble uncrosslinked, relatively high molecular weight polymer actually absorbs or simply immobilizes a liquid is not considered to be important for purposes of the present invention as long as the effectively entangled, solvent-insoluble uncrosslinked, relatively high molecular weight polymer effectively impedes the movement or flow of a liquid so as to exhibit the desired liquid handling properties described herein, such as, for example, Free Swell, Absorbency Under Load, and Centrifuge Retention Capacity.

It has now been discovered that an absorbent composition comprising an uncrosslinked, relatively high molecular weight polymer may be prepared that exhibits a relatively high total liquid absorption or immobilization capacity. In one embodiment of the present invention, the absorbent composition will consist essentially of an uncrosslinked, relatively high molecular weight polymer.

As used herein, the term "comprising" is intended to be synonymous with "including", "having", "containing", or "characterized by", and is intended to be inclusive or open-ended and is not intended to exclude additional, unrecited elements or method steps.

In accordance with this invention, the absorbent composition may be prepared by subjecting a solvent soluble, uncrosslinked, relatively high molecular weight polymer to a means to insolubilize the uncrosslinked, relatively high molecular weight polymer such that the absorbent composition exhibits significant and unexpected improvements in its absorbent properties, including improved total liquid absorption, as compared to the properties exhibited by the original, untreated uncrosslinked, relatively high molecular weight polymer alone.

The absorbent composition of the present invention generally comprises an uncrosslinked, relatively high molecular weight polymer. Polymers useful in the present invention include polyethylene oxide, poly(acrylic acid), poly(vinyl alcohol), poly(vinyl pyrrolidone), copolymers of such polymers, or mixtures of such polymers. It is desired that such polymers be free from any crosslinking so that such polymers are initially solvent-soluble. As used herein, a material will be considered to be soluble when it dissolves in an excess of solvent to form a solution within about 19 hours, such that the material loses its initial, typically particulate, form and becomes essentially molecularly dispersed throughout the solvent mixture.

As used herein, the term "solvent-swellable, solvent-insoluble" is meant to refer to a material that, when exposed to an excess of a solvent, swells to its equilibrium volume but does not substantially dissolve into the solvent within about 19 hours. As such, a solvent-swellable, solvent-insoluble material generally retains its original identity or physical structure, but in a highly expanded state, during the absorption or immobilization of the solvent and, thus, must have sufficient physical integrity to resist flow and fusion with neighboring particles. Because a polymer useful in the present invention is not crosslinked but is a relatively high molecular weight polymer that is treated by a means to become effectively entangled, it should be appreciated that some portion of the relatively high molecular weight polymer may still be soluble in a solvent although a significant portion of the relatively high molecular weight polymer has become effectively insoluble in the solvent.

One property of the uncrosslinked polymer which has been found to be relevant to its effectiveness in providing a desired amount of liquid-absorbing or liquid-immobilizing capacity to the absorbent composition is the polymer's molecular weight. In general, an uncrosslinked polymer with a higher molecular weight will exhibit a higher liquid-absorbing or liquid-immobilizing capacity as compared to a uncrosslinked polymer with a lower molecular weight.

The uncrosslinked polymer useful in the absorbent composition may generally have a wide range of molecular weights. However, it has been discovered that in order to be effective to provide a desired amount of liquid-absorbing capacity to the absorbent composition, the uncrosslinked polymers useful in the present invention must have a weight average molecular weight that is above a minimum value. Nonetheless, a wide range of molecular weights is generally suitable for use in the present invention. Uncrosslinked polymers suitable for use in the present invention will beneficially have a weight average molecular weight greater than about 500,000, more beneficially greater than about 750,000, even more beneficially greater than about 1,000,000, suitably greater than about 1,500,000, more suitably greater than about 2,000,000, even more suitably greater than about 3,000,000, and up to about 20,000,000. In certain embodiments of the present invention, uncrosslinked polymers suitable for use in the present invention will beneficially have a weight average molecular weight that is in the range of between about 1,000,000 to about 20,000,000, more beneficially between about 1,500,000 to about 20,000,000, even more beneficially between about 2,000,000 to about 20,000,000, suitably between about 3,000,000 to about 20,000,000, more suitably between about 1,500,000 to about 15,000,000, even more suitably between about 3,000,000 to about 12,000,000. Desirably, the weight average molecular weight of a polymer is determined by using standard rheological measurement techniques.

The uncrosslinked, high molecular weight polymers useful in the present invention, if in their original or untreated form, are soluble in a solvent and, thus, substantially incapable of absorbing or immobilizing a liquid. It has been discovered, however, that if such uncrosslinked, high molecular weight polymers are treated by a means to effectively insolubilize the uncrosslinked, relatively high molecular weight polymer, such polymer may then surprisingly exhibit significant and unexpected improvements in its liquid absorbent or liquid immobilization properties, including improved total liquid absorption or immobilization, as compared to the properties exhibited by the original, untreated uncrosslinked, relatively high molecular weight polymer.

In the present invention, even after being treated by a means to effectively insolubilize the uncrosslinked, relatively high molecular weight polymer, such polymer will still remain uncrosslinked. This is in contrast to known absorbent materials which generally require that such absorbent materials be crosslinked so as to provide the material with the insolubility needed to provide the desired liquid absorbent properties. While not wishing to be bound hereby, it is believed that the means to effectively insolubilize uncrosslinked, relatively high molecular weight polymers result in the polymers becoming sufficiently entangled so that such polymers are effectively solvent-insoluble within a desired time frame, which in the present invention is about 19 hours. The methods used to synthesize high molecular weight solvent-soluble polymers typically result in powders consisting of individual molecules, which dissolve readily in a large excess of solvent as the individual polymer chains become wet or hydrate. On drying such a solution, however, the long polymer chains dry as a highly entangled mass and, upon being added to a solvent again, solvate but are unable to spontaneously separate and, thus, truly dissolve during the limited time in which, for example, a disposable absorbent product comprising the polymer would be worn. A macroscopic analogy would be strands of spaghetti, which are straight and easily separable until cooking, whereupon the spaghetti strands physically entangle and individual strands cannot easily be separated. The effect of increasing the molecular weight of a polymer can be considered as increasing the length of individual spaghetti strands. If individual strands are long enough, they are for all practicable purposes inseparable, or, on the molecular level, insoluble.

The present invention provides an absorbent composition that may be prepared simply and with a minimum of materials and additives so as to reduce the overall cost of preparing the absorbent composition as well as to reduce the potential deleterious effect that such additives might have on the overall absorbent properties of the absorbent composition. The present invention also provides an absorbent composition that may be prepared from readily-available materials since such may reduce the overall cost of preparing the absorbent composition.

It has been found that the effectively solvent-insoluble yet uncrosslinked, relatively high molecular weight polymer may be prepared by a variety of processes. One process of effectively insolubilizing the uncrosslinked, relatively high molecular weight polymer is to prepare a mixture of the solvent-soluble, uncrosslinked, relatively high molecular weight polymer and a solvent in which the polymer is soluble. Such a mixture generally comprises from about 0.01 to about 90 weight percent, beneficially from about 0.1 to about 30 weight percent, and suitably from about 2 to about 25 weight percent, based on total mixture weight, of the uncrosslinked, relatively high molecular weight polymer. The mixture generally comprises from about 99.99 to about 10 weight percent, beneficially from about 99.9 to about 70 weight percent, and suitably from about 98 to about 75 weight percent, based on total mixture weight, of the solvent.

The dissolution of the uncrosslinked, relatively high molecular weight polymer into a mixture is believed to result in entanglement of individual segments of the uncrosslinked, relatively high molecular weight polymer with each other. Such entanglement results in the polymer chains interpenetrating one another in the mixture, so that a random, coil-entangled molecular configuration occurs which is believed to result in the effective insolublization of the polymer. To allow for effective entanglement of individual segments of the uncrosslinked, relatively high molecular weight polymer with each other, the mixture is suitably allowed to form a stable, homogeneous mixture at equilibrium prior to additional treatment steps to ensure effective dissolution of the uncrosslinked, relatively high molecular weight polymer into the solvent.

The uncrosslinked, relatively high molecular weight polymer is typically dissolved in a solvent comprising at least about 30 weight percent water, beneficially about 50 weight percent water, suitably about 75 weight percent water, and more suitably about 100 weight percent water. However, depending on the uncrosslinked, relatively high molecular weight polymer being used, other solvents may be suitably used. Such other suitable solvents include ketones such as acetone or methyl ethyl ketone, alcohols such as methanol or ethanol, and heteroatom oxide solvents such as dimethylsulfoxide or hexamethylphosphoramide. In addition, non-solvent liquids may also be present in the mixture. However, the use or presence of such other non-solvents may impede the formation of a homogeneous mixture such that the uncrosslinked, relatively high molecular weight polymer chains do not effectively dissolve into the solution and interpenetrate one another.

However, in certain instances, the use or presence of a non-solvent liquid may assist in the formation of a homogeneous mixture such that the uncrosslinked, relatively high molecular weight polymer chains do effectively dissolve into the solution and interpenetrate one another. For example, if an uncrosslinked, relatively high molecular weight polymer is first mixed with a non-solvent liquid and effectively stirred or blended, the uncrosslinked, relatively high molecular weight polymer may be effectively dispersed throughout the non-solvent liquid such that when an effective amount of a solvent is added to the mixture of the uncrosslinked, relatively high molecular weight polymer and the non-solvent liquid, the uncrosslinked, relatively high molecular weight polymer more effectively dissolves into the solvent such that the individual uncrosslinked, relatively high molecular weight polymer chains more effectively interpenetrate one another. In such a situation, the use of the non-solvent liquid may allow for the preparation of solutions or mixtures that comprise a higher concentration of the uncrosslinked, relatively high molecular weight polymer.

In one embodiment of the present invention, polyethylene oxide may first be effectively mixed with and effectively dispersed into a non-solvent, such as methanol. Then, an effective amount of a solvent, such as water, is added to the polyethylene oxide and methanol mixture. The polyethylene oxide, methanol, and water mixture is then effectively mixed to ensure effective dissolution of the polyethylene oxide into the water. In particular, about 17 parts, by weight, of polyethylene oxide may first be effectively mixed with and effectively dispersed into about 29 parts, by weight, of methanol. About 54 parts, by weight, of water is then added to the polyethylene oxide and methanol mixture and the total mixture is then effectively mixed to ensure effective dissolution of the polyethylene oxide into the water.

The mixture of an uncrosslinked, relatively high molecular weight polymer and a solvent can generally be formed at any temperature at which the uncrosslinked, relatively high molecular weight polymer is soluble in the solvent. Generally, such temperatures will be within the range of from about 10° C. to about 100° C. As a general rule, it is suitable to form the mixture with agitation, stirring, or blending, although such agitation, stirring, or blending should not be done with excessive force since such may degrade the polymer. Equipment for achieving such agitation, stirring, or blending are well known in the art and include simple blenders and mixers.

If desired, the mixture of an uncrosslinked, relatively high molecular weight polymer and a solvent may be processed to prepare desired forms of the uncrosslinked, relatively high molecular weight polymer and/or the mixture of the uncrosslinked, relatively high molecular weight polymer and a solvent. For example, extrusion, casting, or other known preparation techniques may be used to prepare films or sheets. If a film is prepared from the mixture of an uncrosslinked, relatively high molecular weight polymer and a solvent, the prepared film may be stretched in order to increase the surface area of the resulting structure, which may be a film or a highly fibrous structure. Increasing the surface area of a film or a fibrous network may allow the solvent and, if used, any non-solvent, to evaporate or otherwise be removed more quickly. A prepared film may be stretched either uniaxially, which may result in a fibrous network with an orientation of the fibers in the fibrous network in the direction of the stretching, or biaxially.

Methods for making fibers are also well known and need not be described here in detail. As one example, a polymer solution may be melt spun or solution spun to prepare a continuous filament, such as spunbond or meltblown, and non-continuous filament, such as staple or short-cut fibers. To form a spunbond or meltblown fiber, generally, a polymer solution is extruded and fed to a distribution system where the polymer solution is introduced into a spinneret plate. The spun fiber is then cooled, solidified, and drawn by an aerodynamic or liquid system, to be formed into a conventional nonwoven. Meanwhile, to produce short-cut or staple fiber rather than being directly formed into a nonwoven structure the spun fiber is cooled, solidified, and drawn, generally by a mechanical rolls system, to an intermediate filament diameter and collected. Subsequently, the fiber may be "cold drawn" at a temperature below its softening temperature, to the desired finished fiber diameter and crimped or texturized and cut into a desirable fiber length.

After forming a mixture of uncrosslinked, relatively high molecular weight polymer and solvent, the uncrosslinked, relatively high molecular weight polymer is recovered from the mixture. Any method of recovering the uncrosslinked, relatively high molecular weight polymer from the mixture, without unacceptably deteriorating the absorption or immobilization characteristics of the uncrosslinked, relatively high molecular weight polymer, is suitable for use in the present invention. Examples of such methods include evaporative drying, freeze drying, precipitation, and critical point drying.

As used herein, recovery of the uncrosslinked, relatively high molecular weight polymer from the preparation mixture is meant to represent that substantially all of the solvent and, if used, any non-solvent is separated from the uncrosslinked, relatively high molecular weight polymer prior to additional treatment steps. It will be appreciated, however, that even after removal of substantially all of the solvent and, if used, any non-solvent, a small amount of solvent and, if used, any non-solvent may remain entrapped within the structure of the entangled, uncrosslinked, relatively high molecular weight polymer. The amount of solvent and, if used, any non-solvent remaining entrapped within the structure of the uncrosslinked, relatively high molecular weight polymer will typically depend on the method and conditions under which the uncrosslinked, relatively high molecular weight polymer is recovered. Generally, less than about 15 weight percent, beneficially less than about 10 weight percent, and suitably less than about 5 weight percent, of the original weight amount of solvent and, if used, any non-solvent in the preparation mixture will remain entrapped within the recovered uncrosslinked, relatively high molecular weight polymer.

Suitably, the uncrosslinked, relatively high molecular weight polymer is recovered from the mixture with evaporative drying. As a general rule, the uncrosslinked, relatively high molecular weight polymer can be recovered by evaporative drying at a temperature within the range of from about 10° C. to about 100° C., and suitably from about 50° C. to about 80° C. Naturally, higher temperatures can be employed if the mixture is placed under pressure. Lower temperatures can be employed if the mixture is placed under a vacuum.

Other methods of recovery include precipitation in which a precipitating agent, such as methanol, ethanol or acetone when water is used as the solvent, is added to the mixture of uncrosslinked, relatively high molecular weight polymer and solvent to precipitate the uncrosslinked, relatively high molecular weight polymer out of the mixture. The uncrosslinked, relatively high molecular weight polymer can then be recovered by filtration. If precipitation is used to recover the uncrosslinked, relatively high molecular weight polymer, it may be desirable to wash the recovered uncrosslinked, relatively high molecular weight polymer to remove the precipitating agent.

Many uncrosslinked, relatively high molecular weight polymers exhibit an upper solution temperature above which an uncrosslinked, relatively high molecular weight polymer becomes insoluble in a solvent being used. For those uncrosslinked, relatively high molecular weight polymers which do exhibit an upper solution temperature, another suitable method of recovery includes raising the temperature of a mixture comprising the entangled but uncrosslinked, relatively high molecular weight polymers until the polymer precipitates out of the solvent.

Depending on the form in which the uncrosslinked, relatively high molecular weight polymer is recovered, it may be necessary or desirable to alter the form of the uncrosslinked, relatively high molecular weight polymer. For example, if evaporative drying is employed, the uncrosslinked, relatively high molecular weight polymer may be recovered in the form of a film or sheet. It may be desirable to comminute the film or sheet material into particles or flakes of material.

The form of the recovered uncrosslinked, relatively high molecular weight polymer desired will depend to a large extent on the use for which it is intended. When the uncrosslinked, relatively high molecular weight polymer is intended for use in disposable absorbent products, it is generally desired that the entangled but uncrosslinked, relatively high molecular weight polymer be in the form of a discrete particle, a fiber, a fibrous web, a film, or a flake. When in the form of a particle, it is generally desired that the particle have a maximum cross-sectional dimension within the range from about 50 micrometers to about 2,000 micrometers, suitably within the range from about 100 micrometers to about 1,000 micrometers, beneficially within the range from about 300 micrometers to about 600 micrometers.

Another process that may be used to effectively insolubilize the uncrosslinked, relatively high molecular weight polymer is to use a melt forming process. In one embodiment of such a process, an uncrosslinked, relatively high molecular weight polymer, suitably in the form of a powder or particulates, is raised above the melting point of the polymer through a combination of heat and pressure, allowing for insolublization through entanglement of the polymer without the use of a solvent. Heating and compressing the uncrosslinked, relatively high molecular weight polymer between, for example, plates coated with tetrafluoroethylene polymer can be used to produce a free standing film with desirable absorbent properties, while heating the uncrosslinked, relatively high molecular weight polymer on, for example, a tissue substrate will provide a strong sheet which can be rolled and unrolled and which will provide desirable absorbent properties.

When a melt forming process is used, the solvent soluble, uncrosslinked polymer is treated at a temperature that is desirably between about 10° C. to about 500° C., more desirably between about 10° C. to about 300° C., even more desirably between about 10° C. to about 250° C., beneficially between about 20° C. to about 250° C., more beneficially between about 20° C. to about 200° C., even more beneficially between about 50° C. to about 200° C., suitably between about 20° C. to about 175° C., more suitably between about 20° C. to about 1 50° C., even more suitably between about 20° C. to about 125° C.

When a melt forming process is used, the solvent soluble, uncrosslinked polymer is treated at a pressure that is desirably between about 100 pounds per square inch (about 0.689 microPascals) to about 10,000 pounds per square inch (about 68.95 microPascals), more desirably between about 250 pounds per square inch (about 1.72 microPascals) to about 7,500 pounds per square inch (about 51.71 microPascals), and even more desirably between about 500 pounds per square inch (about 3.45 microPascals) to about 5,000 pounds per square inch (about 34.47 microPascals).

Another process which can be used to physically insolubilize the uncrosslinked, relatively high molecular weight polymer is to introduce a complexing agent which will form an insoluble physical complex (such as an acid-base complex). An example of such a complex is seen in the interaction of polyethylene oxide and poly(acrylic acid). Polyethylene oxide polymer, suitably in the form of a powder or particulates, can be rendered swellable but insoluble by adding up to about ten weight percent of poly(acrylic acid) polymer, suitably in the form of a powder or particulates, mixing well, placing the mixed polymers, suitably in the form of a powder or particulate mixture, on a suitable substrate and allowing interaction either through heat, such as by pressing on a heated platen, or by misting with a liquid such as water to allow the acid-base complex to form, followed by drying. Heating the mixture of polymers between, for example, plates coated with tetrafluoroethylene polymer can be used to produce a free standing film with desirable absorbent properties, while heating the mixture of polymers on, for example, a tissue substrate will provide a strong sheet which can be rolled and unrolled and which will provide desirable absorbent properties.

Once the solvent-soluble, uncrosslinked, relatively high molecular weight polymer has been subjected to a means to insolubilize the uncrosslinked, relatively high molecular weight polymer, the solvent-insoluble, uncrosslinked, relatively high molecular weight polymer has been found to exhibit significant and unexpected improvements in its liquid absorbent or liquid immobilization properties, including improved total liquid absorption or liquid immobilization, as compared to the properties exhibited by the original, untreated, solvent-soluble uncrosslinked, relatively high molecular weight polymer alone.

The absorbent composition of the present invention suitably has the ability to absorb or immobilize a liquid under a negligible applied load or restraining force, herein referred to as Free Swell (FS). The method by which the Free Swell value is determined is set forth below in connection with the examples. The Free Swell values determined as set forth below and reported herein refer to the amount in grams of a test liquid a gram of a material contained in a stock teabag can absorb or immobilize in a specified time. In one embodiment of the present invention, the Free Swell value of a material is determined using water as the test liquid. In another embodiment of the present invention, the Free Swell value of a material is determined using a 0.9 weight percent solution of sodium chloride in distilled water as the test liquid. Unless otherwise specified, the time period used to determine the Free Swell value of a material is about 19.0 hours (or about 1140 minutes). However, for comparative purposes, other time periods may also be used to determine the Free Swell value of a material.

As a general rule, it is desired that the absorbent composition of the present invention exhibits a Free Swell value of at least about 15, beneficially of at least about 20, suitably of at least about 25, more suitably of at least about 30, and up to about 200 grams of test liquid per gram of absorbent composition (g/g). Thus, in one embodiment of the present invention, it is desired that the absorbent composition of the present invention exhibits a Free Swell value of at least about 15, beneficially of at least about 20, suitably of at least about 25, more suitably of at least about 30, and up to about 200 grams of water per gram of absorbent composition wherein the time period used to determine the Free Swell value is about 19.0 hours. In another embodiment, it is desired that the absorbent composition of the present invention exhibits a Free Swell value of at least about 15, beneficially of at least about 20, suitably of at least about 25, more suitably of at least about 30, and up to about 200 grams of a 0.9 weight percent solution of sodium chloride in distilled water per gram of absorbent composition wherein the time period used to determine the Free Swell value is about 19.0 hours.

In one embodiment of the present invention, the absorbent composition has the ability to absorb or immobilize a liquid while the absorbent composition is under an external pressure or load, herein referred to as Absorbency Under Load (AUL). Synthetic polymeric materials, such as sodium polyacrylates, having a generally high ability to absorb a liquid while under a load, have been found to minimize the occurrence of gel-blocking when incorporated in absorbent products. The method by which the Absorbency Under Load is determined is set forth below in connection with the examples. The Absorbency Under Load values determined as set forth below and reported herein refer to the amount in grams of a test liquid a gram of a material can absorb or immobilize in a specified time under a load of about 0.3 pound per square inch (psi) (about 2.07 kiloPascals). In one embodiment of the present invention, the Absorbency Under Load value of a material is determined using water as the test liquid. In another embodiment of the present invention, the Absorbency Under Load value of a material is determined using a 0.9 weight percent solution of sodium chloride in distilled water as the test liquid. Unless otherwise specified, the time period used to determine the Absorbency Under Load value of a material is about 19.0 hours (or about 1140 minutes). However, for comparative purposes, other time periods may also be used to determine the Absorbency Under Load value of a material.

As a general rule, it is desired that the absorbent composition of the present invention has an Absorbency Under Load value, for a load of about 0.3 psi (about 2.07 kiloPascals), of at least about 15, beneficially of at least about 20, suitably of at least about 25, and up to about 100 grams of test liquid per gram of absorbent composition. Thus, in one embodiment of the present invention, it is desired that the absorbent composition of the present invention exhibits an Absorbency Under Load value of at least about 15, beneficially of at least about 20, suitably of at least about 25, and up to about 100 grams of water per gram of absorbent composition wherein the time period used to determine the Absorbency Under Load value is about 19.0 hours. In another embodiment, it is desired that the absorbent composition of the present invention exhibits an Absorbency Under Load value of at least about 15, beneficially of at least about 20, suitably of at least about 25, and up to about 100 grams of a 0.9 weight percent solution of sodium chloride in distilled water per gram of absorbent composition wherein the time period used to determine the Absorbency Under Load value is about 19.0 hours.

In one embodiment of the present invention, the absorbent composition has the ability to retain a liquid within its structure while the absorbent composition is subjected to a centrifugal force, herein referred to as Centrifuge Retention Capacity (CRC). The method by which the Centrifuge Retention Capacity is determined is set forth below in connection with the examples. The Centrifuge Retention Capacity values determined as set forth below and reported herein refer to the amount in grams of a test liquid a gram of a material can retain after absorbing or immobilizing the test liquid in a specified time under essentially no load and then being centrifuged for about 3 minutes at about 290 times the gravitational force. In one embodiment of the present invention, the Centrifuge Retention Capacity value of a material is determined using water as the test liquid. In another embodiment of the present invention, the Centrifuge Retention Capacity value of a material is determined using a 0.9 weight percent solution of sodium chloride in distilled water as the test liquid. Unless otherwise specified, the time period used to determine the Centrifuge Retention Capacity value of a material is about 19.0 hours (or about 1140 minutes). However, for comparative purposes, other time periods may also be used to determine the Centrifuge Retention Capacity value of a material.

As a general rule, it is desired that the absorbent composition has a Centrifuge Retention Capacity value of at least about 8, beneficially of at least about 10, more beneficially of at least about 12, suitably of at least about 14, more suitably of at least about 16, and up to about 100 grams of test liquid per gram of absorbent composition. Thus, in one embodiment of the present invention, it is desired that the absorbent composition of the present invention exhibits a Centrifuge Retention Capacity value of at least about 8, beneficially of at least about 10, more beneficially of at least about 12, suitably of at least about 14, more suitably of at least about 16, and up to about 100 grams of water per gram of absorbent composition wherein the time period used to determine the Centrifuge Retention Capacity value is about 19.0 hours. In another embodiment, it is desired that the absorbent composition of the present invention exhibits a Centrifuge Retention Capacity value of at least about 8, beneficially of at least about 10, more beneficially of at least about 12, suitably of at least about 14, more suitably of at least about 16, and up to about 100 grams of a 0.9 weight percent solution of sodium chloride in distilled water per gram of absorbent composition wherein the time period used to determine the Centrifuge Retention Capacity value is about 19.0 hours.

While the principal components of the absorbent composition of the present invention have been described in the foregoing, such absorbent composition is not limited thereto and can include other components not adversely affecting the absorbent composition having the desired absorbent properties. Exemplary materials which could be used as additional components would include, without limitation, pigments, antioxidants, stabilizers, surfactants, waxes, flow promoters, solid solvents, particulates, and materials added to enhance processability of the absorbent composition.

The absorbent composition of the present invention is suitable for use in disposable absorbent products such as personal care products, such as diapers, training pants, baby wipes, feminine care products, adult incontinent products; and medical products, such as wound dressings or surgical gowns or drapes.

In one embodiment of the present invention, a disposable absorbent product is provided, which disposable absorbent product comprises a liquid-permeable topsheet, a backsheet attached to the topsheet, and an absorbent structure positioned between the topsheet and the backsheet wherein the absorbent structure comprises the absorbent composition of the present invention, wherein the absorbent composition exhibits desired absorbent properties.

Disposable absorbent products, according to all aspects of the present invention, are generally subjected during use to multiple insults of a liquid, such as a body liquid such as urine, feces, blood, or menses, or other liquids such as water or a saline solution. Accordingly, the disposable absorbent products are desirably capable of absorbing multiple insults of a liquid in quantities to which the absorbent products and structures will be exposed during use. The insults are generally separated from one another by a period of time.

For a disposable absorbent product that is intended to be used to absorb a liquid such as blood or menses, it is generally desired that the relatively high molecular weight polymer that is used be a non-ionic polymer, such as polyethylene oxide. This is because non-ionic polymers have been found to generally absorb liquids such as blood or menses better than ionic polymers such as conventional polyacrylate superabsorbents. This is believed to be due to the presence of proteins or red blood cells which are believed to adhere to or become associated with the ionic groups of an ionic polymer, thereby inhibiting the absorption of the blood or menses by the ionic polymer. Furthermore, non-ionic polymers, such as polyethylene oxide, have been found to generally exhibit relatively similar absorptive capacities for different liquids such as water, saline, and blood. In contrast, ionic polymers generally exhibit relatively different absorptive capacities for different liquids such as water, saline, and blood.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

The absorbent composition is typically present in an absorbent structure in conjunction with a fibrous matrix. A fibrous matrix may take the form of, for example, a batt of comminuted wood pulp fluff, a tissue layer, a hydroentangled pulp sheet, or a mechanically softened pulp sheet. Suitably, the fibrous matrix is formed so as to constrain or entrap the absorbent composition within, or onto, its structure. The absorbent composition may be incorporated into or onto the fibrous matrix either during or after the formation of the general form of the fibrous matrix. A fibrous matrix useful in the present invention may be formed by an airlaying process or a wet-laid process, or by essentially any other process known to those skilled in the art for forming a fibrous matrix.

In one embodiment of the present invention, a liquid impervious nonwoven material, such as certain meltblown materials, is substantially coated with a film or nonwoven layer of a solvent insoluble, uncrosslinked, relatively high molecular weight polymer of the present invention. The resulting absorbent structure, or composite fabric, will thereby comprise a liquid absorbing or liquid immobilizing layer attached to or bonded to a liquid impervious layer. In a further embodiment, the liquid impervious nonwoven material may further comprise a cloth-like material, such as a spunbond material or layer, principally for desired aesthetic purposes for an overall disposable absorbent product.

Such a composite fabric could be prepared, for example, by extruding or solution spinning a mixture of an uncrosslinked, relatively high molecular weight polymer and a solvent directly onto a liquid impervious nonwoven material. Desirably, the mixture of the uncrosslinked, relatively high molecular weight polymer and the solvent is allowed to dry such that a solvent insoluble, uncrosslinked, relatively high molecular weight polymer is recovered and is adhered to the liquid impervious nonwoven material. Depending on how the mixture of an uncrosslinked, relatively high molecular weight polymer and a solvent is applied to a substrate and then allowed to dry, the resulting film or fibrous network may contract during drying. If such contraction occurs, the composite fabric may become wrinkled or bend inwards toward the side of the application of the uncrosslinked, relatively high molecular weight polymer.

Suitably, no separate adhesive material is needed to sufficiently bond the solvent insoluble, uncrosslinked, relatively high molecular weight polymer to the liquid impervious nonwoven material. However, if greater levels of bonding of the solvent insoluble, uncrosslinked, relatively high molecular weight polymer to the liquid impervious nonwoven material is desired, further bonding methods, such as thermal or ultrasonic bonding methods, may be used.

By carefully selecting a specific uncrosslinked, relatively high molecular weight polymer and a specific liquid impervious nonwoven material, the bonding achieved between the polymer and the nonwoven material may be greatly enhanced. In general, if the uncrosslinked, relatively high molecular weight polymer is extruded or solution spun onto a hydrophobic nonwoven material, the adhesion of the uncrosslinked, relatively high molecular weight polymer to the nonwoven material may be relatively poor. In contrast, if a hydrophilic nonwoven material is used, the adhesion of the uncrosslinked, relatively high molecular weight polymer to the nonwoven material may be relatively better. A suitable hydrophilic nonwoven material for preparing a composite fabric may be a bonded carded web comprising a majority, such as greater than about 50 weight percent to about 100 weight percent, of rayon fibers and a minority, such as less than about 50 weight percent to about 0 weight percent, of binder fibers such as polyolefin fibers such as polypropylene or polyethylene fibers.

The absorbent composition is typically present in an absorbent structure or product of the present invention in an amount effective to result in the absorbent structure or product being able to absorb a desired amount of liquid. The absorbent composition is beneficially present in an absorbent structure in an amount of from about 1 to about 100 weight percent, suitably in an amount of from about 5 to about 95 weight percent, and more suitably of from about 10 to about 90 weight percent, based on the total weight of the absorbent composition and a substrate in the absorbent structure.

Test Methods
Free Swell

The Free Swell (FS) is a test which measures the amount in grams of a test liquid, such as water or a 0.9 weight percent solution of sodium chloride in distilled water, a gram of a material can absorb or immobilize in a single time interval, or a series of time intervals, under a negligible applied load or restraining force.

Stock teabag material is cut into a 3 inch (about 7.6 centimeter) by 5 inch (about 12.7 centimeter) rectangle and folded in half to form a 2.5 inch (about 6.4 centimeters) by 3 inch (about 7.6 centimeters) rectangle with the sealable face inward. Two of the three open sides are heat sealed with the inside edge of the seal about 0.25 inch (about 0.64 centimeters) from the edge. About 0.2 gram of sample material is placed into a preweighed teabag, and the open end of the teabag is heat sealed. The teabag is submerged in a pan of a test liquid for a designated time interval, removed, allowed to drain on a wire mesh at about a 45 degree angle for about 2 minutes, and then weighed. If a series of time intervals is to be run, the sample is returned to the test liquid until the next time interval. After the final interval, the teabag is again allowed to drain on the wire mesh for about 2 minutes and then weighed again. The teabag is then allowed to dry and then weighed again. A blank test is also run by wetting under similar conditions an empty teabag which had also been placed in the test liquid. The weight of test liquid absorbed or immobilize per gram of dry sample material is calculated from the data obtained, and this is expressed as the Free Swell value in terms of grams of test liquid retained per gram of dry sample material. Generally, three similar samples of a material are evaluated at the same time and their results averaged to obtain a reportable Free Swell value for the material.

Absorbency Under Load

The Absorbency Under Load (AUL) is a test which measures the amount in grams of a test liquid, such as water or a 0.9 weight percent solution of sodium chloride in distilled water, a gram of a material can absorb or immobilize in a single time interval, or a series of time intervals, while under an applied load or restraining force of about 0.3 pound per square inch (about 2.07 kilopascals).

To evaluate Absorbency Under Load, a material sample is sieved to obtain a 40 to 50 Tyler-equivalent mesh (about 420 micrometers to about 300 micrometers) range particle size. Into a cup, consisting of a rigid plastic tube having a 1 inch (about 2.5 centimeter) inner diameter, an outside diameter of 1.25 inches (about 3.2 centimeter), and closed at one end with a 100 Tyler-equivalent mesh (about 150 micrometers) screen, was placed in a monolayer about 0.16 gram of the sieved material sample. The sample is then covered with a plastic spacer disc, weighing about 4.4 grams, which is slightly smaller than the inside diameter of the sample cup and serves to protect the sample from being disturbed during the test. A weight, weighing about 100 grams, was placed onto the spacer disc, thereby applying a load of about 0.3 pound per square inch (about 2.07 kiloPascals) to the material sample. The total weight of the cup, sample material, and weight was then determined. The cup was then placed into a dish with sufficient test liquid to flood the screen and contact the material sample. The material sample was allowed to absorb the liquid under the weight load for a time interval. After the time interval, the cup was removed from the dish and the bottom of the cup was blotted on fresh paper toweling, to remove excess liquid, for about 2 minutes. The cup, swollen material sample, and weight was then reweighed. Any increase in weight was attributed to the material sample swelling with the test liquid. The process is repeated for as many time intervals as needed. The weight of test liquid absorbed or immobilized after the final time interval is the Absorbency Under Load value expressed as grams of test liquid absorbed or immobilized per gram of material sample. Generally, three similar samples of a material are evaluated at the same time and their results averaged to obtain a reportable Absorbency Under Load value for the material.

Centrifuge Retention Capacity

The Centrifuge Retention Capacity (CRC) is a test which measures the amount in grams of a test liquid, such as water or a 0.9 weight percent solution of sodium chloride in distilled water, a gram of a material can absorb or immobilize in a single time interval, or a series of time intervals, after being subjected to a centrifugal force for a period of time.

Stock teabag material is cut into a 3 inch (about 7.6 centimeter) by 5 inch (about 12.7 centimeter) rectangle and folded in half to form a 2.5 inch (about 6.4 centimeters) by 3 inch (about 7.6 centimeters) rectangle with the sealable face inward. Two of the three open sides are heat sealed with the inside edge of the seal about 0.25 inch (about 0.64 centimeters) from the edge. About 0.2 gram of sample material is placed into a preweighed teabag, and the open end of the teabag is heat sealed. The teabag is submerged in a pan of test liquid for a time interval, removed, allowed to drain on a wire mesh at about a 45 degree angle for about 2 minutes, centrifuged for about 3 minutes at 290 times the gravitational force and then weighed. If a series of time intervals is to be run, the sample is returned to the test liquid until the next time interval. After each time interval, the teabag is again allowed to drain on the wire mesh for about 2 minutes, again centrifuged for about 3 minutes at 290 times the gravitational force, and then weighed again. After the final time interval, the teabag is then allowed to dry and then weighed again. A blank test is also run by centrifuging under similar conditions an empty teabag which had also been placed in the test liquid. The weight of test liquid retained per gram of dry sample material after centrifuging is calculated from the data obtained, and this is expressed as the Centrifuge Retention Capacity value in terms of grams of test liquid retained per gram of dry sample material.

EXAMPLE

Example 1

Uncrosslinked samples of polyethylene oxide (PEO), differing in weight average molecular weight, were obtained from Union Carbide Corporation of Danbury, Conn. Weight average molecular weight (MW) information on these polymers was obtained from Union Carbide Corporation.

About 5.0 grams of a polyethylene oxide sample, in the form of a powder, was introduced into a dry 1500 milliliter beaker. A Caframo RZR 50 mixer, equipped with a stirring shaft with two 1 inch [about 2.5 centimeters (cm)] propeller blades set about one inch (about 2.5 cm) apart and set to a speed of approximately 60 revolutions per minute (rpm), was used to get the powder moving slowly in the bottom of the beaker. About 50 milliliters of reagent grade isopropyl alcohol was added all at once to the stirring powder, producing a slurry of the polyethylene oxide powder. The mixer was accelerated to 600 rpm and about 450 milliliters of deionized water was added all at once to the rapidly stirring slurry. The mixer was slowed to about 60 rpm and the slurry stirred until a clear solution was formed, indicating that dissolution of the polyethylene oxide powder had occurred. The polyethylene oxide was recovered from the solution by pouring the solution into a polyfluoroethylene-lined cookie pan (to increase the surface area of the solution) and then drying the solution overnight in an oven at about 50° C.

The recovered polyethylene oxide was then evaluated for Free Swell (FS) and Centrifuge Retention Capacity (CRC) values. In Table 1, the Free Swell and the Centrifuge Retention Capacity values were determined using a 0.9 weight percent solution of sodium chloride in distilled water. In Table 2, the Free Swell and the Centrifuge Retention Capacity values were determined using distilled water. All values shown for Free Swell and Centrifuge Retention Capacity represent the average of evaluating 3 samples for a particular Sample No.

From Tables 1 and 2, it can be seen that there appears to be an unexpected increase in absorbent capacity, at 19 hours, for insolubilized polyethylene oxide polymers that have a weight average molecular weight that is greater than about 1,000,000. Because of the mechanics of the Free Swell and the Centrifuge Retention Capacity evaluations, the Centrifuge Retention Capacity value is generally considered to be a better indication of liquid truly absorbed within the gel structure of an insolubilized polyethylene oxide polymer.

From Tables 1 and 2, it can also be seen that there appears to be no substantial difference in absorbency, as represented by the Free Swell and the Centrifuge Retention Capacity values at 19 hours, between the use of saline solution and distilled water as the test liquid for the Free Swell and the Centrifuge Retention Capacity evaluations.

TABLE 1

Free Swell and Centrifuge Retention Capacity of Entangled PEO (in saline)

| Sample No. | PEO MW | FS (80 min) | FS (19 hours) | CRC (19 hours) |
|---|---|---|---|---|
| 1 | 8,000,000 | 17.7g/g | 29.3g/g | 20.1g/g |
| 2 | 7,000,000 | 19.5g/g | 30.5g/g | 16.1g/g |
| 3 | 4,000,000 | 21.4g/g | 23.9g/g | 12.9g/g |
| 4* | 1,000,000 | 12.0g/g | −1.7g/g | 0.7g/g |
| 5* | 400,000 | 4.6g/g | −1.1g/g | 0.5g/g |
| 6* | 300,000 | 2.3g/g | −0.4g/g | 0.6g/g |
| 7* | 200,000 | −0.8g/g | −1.0g/g | 0.7g/g |

*Not an example of the present invention.

TABLE 2

Free Swell and Centrifuge Retention Capacity of Entangled PEO (in water)

| Sample No. | PEO MW | FS (80 min) | FS (19 hours) | CRC (19 hours) |
|---|---|---|---|---|
| 1 | 8,000,000 | 19.2g/g | 34.1g/g | 23.8g/g |
| 2 | 7,000,000 | 20.9g/g | 29.3g/g | 18.2g/g |
| 3 | 4,000,000 | 23.5g/g | 20.4g/g | 13.1g/g |
| 4* | 1,000,000 | 8.3g/g | 0.7g/g | 1.0g/g |
| 5* | 400,000 | 5.6g/g | −0.2g/g | 0.1g/g |
| 6* | 300,000 | 3.3g/g | −0.8g/g | 0.2g/g |
| 7* | 200,000 | 0.4g/g | 0.8g/g | 0.7g/g |

*Not an example of the present invention.

Example 2

This example shows that an absorbent composition based on entanglement depends on the degree of entanglement for both its absorbent capacity and the time before it essentially completely dissolves into a liquid.

An uncrosslinked sample of polyethylene oxide (PEO), exhibiting a weight average molecular weight of about 8,000,000, was obtained from Union Carbide Corporation of Danbury, Conn., under the designation PEO WSR-308 polyethylene oxide.

Preparation Method A: About 500 milliliters of deionized water was heated to boiling. After reaching the boiling point, the boiling water was rapidly stirred using a Caframo RZR 50 mixer equipped with a stirring shaft with two 1 inch (about 2.5 cm) propeller blades set about one inch (about 2.5 cm) apart and set to a speed of approximately 600 revolutions per minute (rpm). About 10.0 grams of the polyethylene oxide, in the form of a powder, was introduced rapidly into the vortex created by the stirring shaft. Once the polyethylene oxide powder was visually observed to be substantially uniformly dispersed in the water, the stirring was slowed to about 60 rpm and the solution was allowed to cool. Once the solution became clear, stirring was discontinued. This level of stirring was considered to produce minimal entanglement of the polyethylene oxide polymer.

Extractable PEO %, which represents the weight percent of polyethylene oxide that escapes from the tea bag during the Free Swell evaluation (which is determined by measuring the weight amount of polyethylene oxide that remains in the tea bag after such Free Swell evaluation). As such, the polyethylene oxide prepared by Preparation Method A exhibits a Free Swell value at about 1140 minutes (about 19 hours) in water that is very low. In contrast, the polyethylene oxide prepared by Preparation Method B, wherein the polyethylene oxide is believed to be recovered after extensive entanglement of the polyethylene oxide, exhibits a Free Swell value at about 1140 minutes (about 19 hours) in water that is relatively high.

In Table 3, the Saline Test Liquid represents a 0.9 weight percent solution of sodium chloride in distilled water.

TABLE 3

COMPARISON OF EFFECT OF DEGREE OF ENTANGLEMENT

| Sample No. | Preparation Method | Test Liquid | FS (80 min) | FS (150 min) | FS (1140 min) | CRC (1140 min) | Extractable PEO % (1140 min) |
|---|---|---|---|---|---|---|---|
| 9* | A | Water | 20.2 g/g | 21.4 g/g | 1.7 g/g | 2.0 g/g | 99 |
| 10 | B | Water | 26.5 g/g | 33.7 g/g | 48.2 g/g | 26.8 g/g | 46 |
| 11 | B | Saline | 32.1 g/g | 44.1 g/g | 79.9 g/g | 55.9 g/g | 0 |

*Not an example of the present invention.

The polyethylene oxide was recovered from the solution by pouring the solution into a polyfluoroethylene-lined cookie pan and then drying the solution overnight in an oven at about 50° C.

Preparation Method B: About 500 milliliters of deionized water was heated to boiling. After reaching the boiling point, the boiling water was rapidly stirred using a Caframo RZR 50 mixer equipped with a stirring shaft with two 1 inch (about 2.5 cm) propeller blades set about one inch (about 2.5 cm) apart and set to a speed of approximately 600 revolutions per minute (rpm). About 5.0 grams of the polyethylene oxide, in the form of a powder, was introduced rapidly into the vortex created by the stirring shaft. Once the powder was visually observed to be uniformly substantially uniformly dispersed in the water, the stirring was slowed to about 60 rpm. The slurry was stirred while cooling to about 90° C. in a constant temperature bath. Over time, the polyethylene oxide powder dissolved in the water such that a clear solution was produced at this temperature and stirring was then continued for another 5 minutes. This solution was considered to have been reasonably well entangled. The solution was again raised to boiling, which caused the polyethylene oxide to precipitate, while stirring was continued. The wet polyethylene oxide polymer was recovered by hot filtration, spread on polyfluoroethylene-lined cookie pans to increase the surface area of the wet polymer, and dried at about 50° C. in an oven overnight.

The absorbent capacity of the polymers recovered by these two preparation methods is summarized in Table 3. All values shown for Free Swell, Centrifuge Retention Capacity, and Extractable PEO % represent the average of evaluating 3 samples for a particular Sample No. It can be seen that the polyethylene oxide prepared by Preparation Method A, wherein the polyethylene oxide is believed to be recovered after minimal entanglement of the polyethylene oxide, will essentially completely dissolve in water within about 1140 minutes (about 19 hours), which is represented by the Comparative Example 1

This example is intended to demonstrate that crosslinked materials do not substantially change in absorbent capacity with time, do not dissolve to a substantial extent, and are substantially unaffected in their absorbent capacity by changes in the molecular weight of the starting material, all of which is unlike entangled absorbent materials.

Sample No. 12 used an uncrosslinked sample of polyethylene oxide (PEO), exhibiting a weight average molecular weight of about 8,000,000, obtained from Union Carbide Corporation of Danbury, Conn., under the designation PEO WSR-308 polyethylene oxide. Sample 13 used an uncrosslinked sample of polyethylene oxide, exhibiting a weight average molecular weight of about 4,000,000, obtained from Union Carbide Corporation of Danbury, Conn., under the designation PEO WSR-301 polyethylene oxide.

Solutions of the different polyethylene oxides were prepared using Preparation Method A as described in Example 2. After such preparation, the solutions were placed into separate plastic bags, excess air was squeezed out of each bag, and the bags were sealed. The sealed bags were exposed to about 1.0 Mrad of ionizing radiation from an electron beam source, available from E-Beam Services, Inc., of Cranbury, N.J. The irradiated samples, each of which had formed a radiation crosslinked gel, were removed from the plastic bags and air dried. The recovered, crosslinked polyethylene oxides were evaluated for Free Swell and Centrifuge Retention Capacity and the results are shown in Table 4. All values shown for Free Swell, Centrifuge Retention Capacity, and Extractable PEO % represent the average of evaluating 3 samples for a particular Sample No.

TABLE 4

| Sample No. | Preparation Method | Test Liquid | FS (80 min) | FS (150 min) | FS (1140 min) | CRC (1140 min) | Extractable PEO % (1140 min) |
|---|---|---|---|---|---|---|---|
| 12* | Radiation Crosslinked | Water | 26.7 g/g | 25.6 g/g | 22.7 g/g | 19.1 g/g | 17 |
| 13* | Radiation Crosslinked | Water | 26.4 g/g | 25.5 g/g | 19.7 g/g | 24.7 g/g | 17 |

*Not an example of the present invention.

Example 3

Samples 14 through 28 used an uncrosslinked sample of polyethylene oxide, exhibiting a weight average molecular weight of about 4,000,000, obtained from Union Carbide Corporation of Danbury, Conn., under the designation PEO WSR-301 polyethylene oxide.

For the preparation of Samples 14 through 28, about 5.0 grams of the polyethylene oxide, in the form of a powder, was evenly spread into a 3 inch (about 7.6 cm) circle on a sheet of metal coated with polytetrafluoroethylene. The polyethylene oxide powder was covered with another sheet of metal coated with polytetrafluoroethylene, and pressed in a press, available from Fred S. Carver, Inc., of Menomonee Falls, Wis., with about 14 inch (about 35 cm) long by about 14 inch (about 35 cm) wide heated platens, for about 10 minutes at the temperatures and pressures noted in Tables 5 and 6. The polyethylene oxide powder flowed into a thin film, from which portions were cut and evaluated for Free Swell and Centrifuge Retention Capacity. The results of these evaluations are summarized in Tables 5 and 6. All values shown for Free Swell, Centrifuge Retention Capacity, and Extractable PEO % represent the average of evaluating 3 samples for a particular Sample No.

From Tables 5 and 6 it appears that peak absorbency in water is achieved when a polyethylene oxide sample is pressed at a temperature of about 100° C. Furthermore, similar absorbencies appear to be obtained at a given temperature over pressures ranging from about 500 to about 5000 pounds per square inch (about 351,550 to about 3,515,500 kilograms per square meter). The amount of extractable material exhibited by a polyethylene oxide sample prepared using heat and pressure is generally lower than polyethylene oxide samples prepared by solution entanglement, suggesting that heat and pressure is a particularly effective means of entangling the polyethylene oxide polymer.

The results from Table 6 suggest that relatively higher temperatures may be less effective in polyethylene oxide entanglement, possibly due to degradation of the polyethylene oxide polymer. Individual pressed films were also inhomogeneous such that samples taken from the inside (near the middle of a pressed film) showed different absorbent properties than samples taken from the outside (near the outer edges of a presses film). In Table 6, samples from near the middle of a pressed film are designated "inside", samples from near the outer edges of a pressed film are designated "outside", and those samples taken before the difference was appreciated are designated NR (for not reported).

TABLE 5

ENTANGLEMENT OF POLYETHYLENE OXIDE USING HEAT AND PRESSURE

| Sample No. | Temp. (° C.) | Pressure (psi) | Test Liquid | FS (80 min) | FS (168 min) | FS (1140 min) | CRC (1288.2 min) | Extractable PEO % (1140 min) |
|---|---|---|---|---|---|---|---|---|
| 14 | 20 | 5000 | Water | 12.6 | 17.5 | 18.5 | 13.8 | 0.6 |
| 15 | 75 | 5000 | Water | 14.5 | 18.2 | 19.0 | 14.0 | 0.6 |
| 16 | 100 | 500 | Water | 10.9 | 15.4 | 21.5 | 17.3 | 0.4 |
| 17 | 100 | 2000 | Water | 10.9 | 14.1 | 19.6 | 16.2 | 0.5 |
| 18 | 100 | 5000 | Water | 12.4 | 17.8 | 22.2 | 16.1 | 0.5 |
| 19 | 125 | 5000 | Water | 14.6 | 17.5 | 21.9 | 14.2 | 0.6 |

TABLE 6

EFFECT OF HIGHER TEMPERATURES ON MELT ENTANGLEMENT OF PEO

| Sample No. | Temp. (° C.) | Pressure (psi) | Sample Location | FS (80 min) | FS (19 hour) | CRC (19 hour) | Extractable PEO % (19 hours) |
|---|---|---|---|---|---|---|---|
| 20 | 158 | 2000 | outside | 22.1 g/g | 19.1 g/g | 11.7 g/g | 77 |
| 21 | 158 | 2000 | inside | 6.0 g/g | 19.7 g/g | 15.4 g/g | 46 |
| 22 | 158 | 500 | outside | 19.3 g/g | 17.8 g/g | 12.8 g/g | 64 |
| 23 | 158 | 500 | inside | 15.7 g/g | 20.3 g/g | 14.3 g/g | 60 |
| 24* | 320 | 500 | outside | 6.0 g/g | −1.9 g/g | 1.2 g/g | 103 |
| 25* | 320 | 500 | inside | 8.9 g/g | 5.8 g/g | 4.8 g/g | 84 |
| 26* | 320 | 2000 | NR | 1.9 g/g | 3.2 g/g | 2.7 g/g | 79 |
| 27 | 158 | 5000 | NR | 4.7 g/g | 19.1 g/g | 15.1 g/g | 46 |
| 28* | 320 | 5000 | NR | 7.0 g/g | 5.4 g/g | 5.3 g/g | 83 |

*Not an example of the present invention.

Example 4

In this example, two separate polymers are entangled together through a complexation process. The formation of a complex of two polymers is believed to be a transient interaction and generally fully reversible, unlike the formation of a chemical bond, which is generally permanent and not spontaneously reversible. The particular complexation prepared in this example is that of a polyethylene oxide material and a poly(acrylic acid) material. This example is believed to show that by entangling these two polymers together through the formation of a complex between the ether oxygens of the polyethylene oxide and the carboxylic acid functionality of the poly(acrylic acid) (PAA), the distinctive absorbent properties of each polymer can be simultaneously utilized.

For Samples 29 through 48, the polyethylene oxide used was an uncrosslinked sample of polyethylene oxide (PEO), exhibiting a weight average molecular weight of about 8,000,000, obtained from Union Carbide Corporation of Danbury, Conn., under the designation PEO WSR-308 polyethylene oxide and the poly(acrylic acid) used was an uncrosslinked sample of poly(acrylic acid), exhibiting a weight average molecular weight of about 4,000,000, obtained from Polysciences Inc., of Warrington, Pa.

Mixtures comprising different weight percents of the polyethylene oxide and the poly(acrylic acid) were prepared. The weight percent of the polyethylene oxide present in a sample is shown in Tables 7 and 8.

About 10.0 grams of a mixture of the two polymers were milled in a 0.3 gallon (about 1.14 liter) ball mill for about 4 hours. The ball mill was obtained from VWR Scientific under the designation Roalox alumina fortified mill jar and was half filled with ceramic grinding media available from VWR Scientific under the designation Burundum medium size cylinders. At the end of 4 hours of milling, the polymers were considered to be well mixed and the mixture was in the form of a powder.

About 5.0 grams of the polyethylene oxide/poly(acrylic acid) polymer mixture was evenly spread into a 3 inch (about 7.6 cm) circle on a sheet of metal coated with polytetrafluoroethylene. The polyethylene oxide powder was covered with another sheet of metal coated with polytetrafluoroethylene, and pressed in a press, available from Fred S. Carver, Inc., of Menomonee Falls, Wis., with about 14 inch (about 35 cm) long by about 14 inch (about 35 cm) wide heated platens, for about 10 minutes at about 5000 psi (about 34.47 microPascals) at the temperatures indicated in Tables 7 and 8. The polymer mixture powder flowed into a thin film, from which portions were cut and evaluated for Free Swell and Centrifuge Retention Capacity. The results of these evaluations are summarized in Tables 7 and 8.

For Samples 45 through 48, the samples comprised about 10 weight percent polyethylene oxide polymer and about 90 weight percent partially neutralized poly(acrylic acid) polymer. The poly(acrylic acid) polymer was partially neutralized to increase its absorbency. To achieve such neutralization, the preparation procedure described above was varied in that the poly(acrylic acid) was first combined with an amount of sodium carbonate, obtained from Aldrich Chemical Co. of Milwaukee, Wis., as a granular, reagent grade sodium carbonate to achieve a desired degree of neutralization of the poly(acrylic acid). The poly(acrylic acid) and sodium carbonate were milled together for about two hours before adding the polyethylene oxide. This final mixture was then milled in the ball mill for an additional two hours before pressing the final mixture into a film, using the procedure discussed above, and then evaluating the film for Free Swell and Centrifuge Retention Capacity. The results from these evaluations are summarized in Table 9. All values shown for Free Swell, Centrifuge Retention Capacity, and Extractable PEO % represent the average of evaluating 3 samples for a particular Sample No. However, the Centrifuge Retention Capacity value for Sample No. 40 represents the average of evaluating only 2 samples.

TABLE 7

PEO/PAA COMPLEX ABSORBENCY (IN WATER)

| Sample No. | PEO wt % | FS (80 min) | FS (19 hours) | CRC (19 hours) | Extractable PEO % (19 hours) | Temperature |
|---|---|---|---|---|---|---|
| 29 | 99 | 26.7 g/g | 46.1 g/g | 37.3 g/g | 28 | 23° C. |
| 30 | 98 | 26.3 g/g | 57.1 g/g | 35.0 g/g | 43 | 23° C. |
| 31 | 95 | 22.2 g/g | 63.6 g/g | 49.9 g/g | 20 | 23° C. |
| 32 | 90 | 30.6 g/g | 82.6 g/g | 59.5 g/g | 18 | 23° C. |
| 33 | 99 | 23.3 g/g | 50.2 g/g | 38.1 g/g | 34 | 38° C. |
| 34 | 98 | 27.4 g/g | 56.6 g/g | 37.1 g/g | 41 | 38° C. |
| 35 | 95 | 24.5 g/g | 67.6 g/g | 52.7 g/g | 21 | 38° C. |
| 36 | 90 | 22.9 g/g | 76.4 g/g | 50.4 g/g | 30 | 38° C. |

TABLE 8

PEO/PAA COMPLEX ABSORBENCY (IN SALINE)

| Sample No. | PEO wt % | FS (80 min) | FS (19 hours) | CRC (19 hours) | Extractable PEO % (19 hours) | Temperature |
|---|---|---|---|---|---|---|
| 37 | 99 | 21.5 g/g | 54.3 g/g | 34.0 g/g | 17 | 23° C. |
| 38 | 98 | 18.2 g/g | 46.4 g/g | 34.5 g/g | 3 | 23° C. |
| 39 | 95 | 18.9 g/g | 48.3 g/g | 37.9 g/g | 0 | 23° C. |
| 40 | 90 | 22.3 g/g | 46.5 g/g | 36.4 g/g | 39 | 23° C. |
| 41 | 99 | 19.4 g/g | 49.4 g/g | 31.9 g/g | 14 | 38° C. |
| 42 | 98 | 23.2 g/g | 48.4 g/g | 37.0 g/g | 0 | 38° C. |
| 43 | 95 | 15.8 g/g | 50.1 g/g | 31.8 g/g | 14 | 38° C. |
| 44 | 90 | 17.0 g/g | 44.3 g/g | 29.3 g/g | 15 | 38° C. |

TABLE 9

ABSORBENCY OF PEO AND PARTIALLY NEUTRALIZED PAA COMPLEXES (IN SALINE)

| Sample No. | Neutralization of PAA | FS (80 min) | FS (19 hour) | CRC (19 hour) | Extractable PEO % (19 hours) |
|---|---|---|---|---|---|
| 45 | 15% | 14.9 g/g | 42.8 g/g | 33.9 g/g | 0 |
| 46 | 25% | 27.3 g/g | 61.6 g/g | 30.9 g/g | 26 |
| 47 | 50% | 42.4 g/g | 79.0 g/g | 37.4 g/g | 22 |
| 48 | 75% | 29.7 g/g | 67.6 g/g | 34.4 g/g | 24 |

While the present invention has been described in terms of the specific embodiments described above, numerous equivalent changes and modifications will be clear to those skilled in the art. Accordingly, the specific examples set forth above are not intended to limit in any manner the scope of the invention as set forth in the appended claims.

What is claimed is:

1. An absorbent composition comprising an uncrosslinked polymer, wherein the uncrosslinked polymer has a weight average molecular weight greater than about 1,000,000 and wherein the absorbent composition exhibits a Free Swell value that is at least about 15 grams of water per gram of absorbent composition and a Centrifuge Retention Capacity value that is at least about 8 grams of water per gram of absorbent composition, wherein the time period used to determine both the Free Swell value and the Centrifuge Retention Capacity value is about 19 hours.

2. The absorbent composition of claim 1 wherein the uncrosslinked polymer is selected from the group consisting of polyethylene oxide, poly(acrylic acid), poly(vinyl alcohol), poly(vinyl pyrrolidone), copolymers of such polymers, and mixtures of such polymers.

3. The absorbent composition of claim 2 wherein the uncrosslinked polymer is polyethylene oxide.

4. The absorbent composition of claim 1 wherein the uncrosslinked polymer has a weight average molecular weight greater than about 1,500,000.

5. The absorbent composition of claim 4 wherein the uncrosslinked polymer has a weight average molecular weight greater than about 2,000,000.

6. The absorbent composition of claim 5 wherein the uncrosslinked polymer has a weight average molecular weight greater than about 3,000,000.

7. The absorbent composition of claim 1 wherein the absorbent composition exhibits a Free Swell value that is at least about 20 grams of water per gram of absorbent composition.

8. The absorbent composition of claim 1 wherein the absorbent composition exhibits a Centrifuge Retention Capacity value that is at least about 10 grams of water per gram of absorbent composition.

9. An absorbent composition comprising an uncrosslinked polymer, wherein the uncrosslinked polymer has a weight average molecular weight greater than about 1,000,000 and wherein the absorbent composition exhibits a Free Swell value that is at least about 15 grams of a 0.9 weight percent solution of sodium chloride in distilled water per gram of absorbent composition and a Centrifuge Retention Capacity value that is at least about 8 grams of a 0.9 weight percent solution of sodium chloride in distilled water per gram of absorbent composition, wherein the time period used to determine both the Free Swell value and the Centrifuge Retention Capacity value is about 19 hours.

10. The absorbent composition of claim 9 wherein the uncrosslinked polymer is selected from the group consisting of polyethylene oxide, poly(acrylic acid), poly(vinyl alcohol), poly(vinyl pyrrolidone), copolymers of such polymers, and mixtures of such polymers.

11. The absorbent composition of claim 10 wherein the uncrosslinked polymer is polyethylene oxide.

12. The absorbent composition of claim 9 wherein the uncrosslinked polymer has a weight average molecular weight greater than about 1,500,000.

13. The absorbent composition of claim 12 wherein the uncrosslinked polymer has a weight average molecular weight greater than about 2,000,000.

14. The absorbent composition of claim 13 wherein the uncrosslinked polymer has a weight average molecular weight greater than about 3,000,000.

15. The absorbent composition of claim 9 wherein the absorbent composition exhibits a Free Swell value that is at least about 20 grams of a 0.9 weight percent solution of sodium chloride in distilled water per gram of absorbent composition.

16. The absorbent composition of claim 9 wherein the absorbent composition exhibits a Centrifuge Retention Capacity value that is at least about 10 grams of a 0.9 weight percent solution of sodium chloride in distilled water per gram of absorbent composition.

17. A process for preparing an absorbent composition comprising an uncrosslinked polymer, the process comprising:

a. preparing a mixture of a solvent soluble, uncrosslinked polymer that has a molecular weight greater than about 1,000,000 and a solvent in which the uncrosslinked polymer is soluble, wherein the soluble, uncrosslinked polymer dissolves into the solvent; and b. recovering the uncrosslinked polymer from the mixture, wherein the absorbent composition exhibits a Free Swell value that is at least about 15 grams of water per gram of absorbent composition and a Centrifuge Retention Capacity value that is at least about 8 grams of water per gram of absorbent composition, wherein the time period used to determine both the Free Swell value and the Centrifuge Retention Capacity value is about 19 hours.

18. The process of claim 17 wherein the process further comprises first preparing a mixture of the solvent soluble, uncrosslinked polymer and a non-solvent.

19. The process of claim 17 wherein the solvent comprises water, acetone, methyl ethyl ketone, methanol, ethanol, dimethylsulfoxide, or hexamethylphosphoramide.

20. The process of claim 19 wherein the solvent consists essentially of water.

21. The process of claim 18 wherein the non-solvent comprises methanol.

22. The process of claim 17 wherein the uncrosslinked polymer is recovered from the mixture by a method selected from the group consisting of evaporative drying, freeze drying, precipitation, and critical point drying.

23. A process for preparing an absorbent composition comprising an uncrosslinked polymer, the process comprising:
   a. preparing a mixture of a solvent soluble, uncrosslinked polymer that has a molecular weight greater than about 1,000,000 and a solvent in which the uncrosslinked polymer is soluble, wherein the soluble, uncrosslinked polymer dissolves into the solvent; and
   b. recovering the uncrosslinked polymer from the mixture,
wherein the absorbent composition exhibits a Free Swell value that is at least about 15 grams of a 0.9 weight percent solution of sodium chloride in distilled water per gram of absorbent composition and a Centrifuge Retention Capacity value that is at least about 8 grams of a 0.9 weight percent solution of sodium chloride in distilled water per gram of absorbent composition, wherein the time period used to determine both the Free Swell value and the Centrifuge Retention Capacity value is about 19 hours.

24. The process of claim 23 wherein the process further comprises first preparing a mixture of the solvent soluble, uncrosslinked polymer and a non-solvent.

25. The process of claim 23 wherein the solvent comprises water, acetone, methyl ethyl ketone, methanol, ethanol, dimethylsulfoxide, or hexamethylphosphoramide.

26. The process of claim 25 wherein the solvent consists essentially of water.

27. The process of claim 24 wherein the non-solvent comprises methanol.

28. The process of claim 23 wherein the uncrosslinked polymer is recovered from the mixture by a method selected from the group consisting of evaporative drying, freeze drying, precipitation, and critical point drying.

29. A process for preparing an absorbent composition comprising a solvent insoluble uncrosslinked polymer, the process comprising treating a solvent soluble, uncrosslinked polymer by means of heat and pressure effective to insolublize the uncrosslinked polymer, wherein the absorbent composition exhibits a Free Swell value that is at least about 15 grams of water per gram of absorbent composition and a Centrifuge Retention Capacity value that is at least about 8 grams of water per gram of absorbent composition, wherein the time period used to determine both the Free Swell value and the Centrifuge Retention Capacity value is about 19 hours.

30. The process of claim 29 wherein the solvent soluble, uncrosslinked polymer is treated at a temperature between about 10° C. to about 250° C.

31. The process of claim 29 wherein the solvent soluble, uncrosslinked polymer is treated at a pressure between about 100 pounds per square inch to about 10,000 pounds per square inch.

32. A process for preparing an absorbent composition comprising a solvent insoluble uncrosslinked polymer, the process comprising treating a solvent soluble, uncrosslinked polymer by means of heat and pressure effective to insolublize the uncrosslinked polymer, wherein the absorbent composition exhibits a Free Swell value that is at least about 15 grams of a 0.9 weight percent solution of sodium chloride in distilled water per gram of absorbent composition and a Centrifuge Retention Capacity value that is at least about 8 grams of a 0.9 weight percent solution of sodium chloride in distilled water per gram of absorbent composition, wherein the time period used to determine both the Free Swell value and the Centrifuge Retention Capacity value is about 19 hours.

33. The process of claim 32 wherein the solvent soluble, uncrosslinked polymer is treated at a temperature between about 10° C. to about 250° C.

34. The process of claim 32 wherein the solvent soluble, uncrosslinked polymer is treated at a pressure between about 100 pounds per square inch to about 10,000 pounds per square inch.

35. A process for preparing an absorbent composition comprising a solvent insoluble uncrosslinked polymer, the process comprising complexing a solvent soluble, uncrosslinked polymer with a complexing agent, wherein the absorbent composition exhibits a Free Swell value that is at least about 15 grams of water per gram of absorbent composition and a Centrifuge Retention Capacity value that is at least about 8 grams of water per gram of absorbent composition, wherein the time period used to determine both the Free Swell value and the Centrifuge Retention Capacity value is about 19 hours.

36. The process of claim 35 wherein the uncrosslinked polymer is polyethylene oxide and the complexing agent is poly(acrylic acid).

* * * * *

UNITED STATES PATENT AND TRADEMARK OFFICE
CERTIFICATE OF CORRECTION

PATENT NO. : 6,369,293 B1
DATED : April 9, 2002
INVENTOR(S) : William Grover Reeves et al.

It is certified that error appears in the above-identified patent and that said Letters Patent is hereby corrected as shown below:

<u>Column 1,</u>
Line 3, insert -- This application claims priority from U.S. Provisional Application No. 60/107,066 -- as the first sentence following the title.

Signed and Sealed this

Second Day of March, 2004

JON W. DUDAS
*Acting Director of the United States Patent and Trademark Office*